(12) United States Patent
Dougherty, Jr. et al.

(10) Patent No.: US 8,696,957 B2
(45) Date of Patent: Apr. 15, 2014

(54) METHODS FOR MICROCELLULAR INJECTION MOLDING

(75) Inventors: Eugene P. Dougherty, Jr., Camden-Wyoming, DE (US); Keith Edgett, Middletown, DE (US); Lih-Sheng Turng, Madison, WI (US); Chris Lacey, Cambridge, WI (US); Jungjoo Lee, Madison, WI (US); Patrick J. Gorton, Clifton Park, NY (US); Xiaofei Sun, Madison, WI (US)

(73) Assignee: Eveready Battery Company, Inc, St. Louis, MO (US)

( * ) Notice: Subject to any disclaimer, the term of this patent is extended or adjusted under 35 U.S.C. 154(b) by 491 days.

(21) Appl. No.: 12/879,498

(22) Filed: Sep. 10, 2010

(65) Prior Publication Data

US 2012/0061870 A1    Mar. 15, 2012

(51) Int. Cl.
*B29C 45/46* (2006.01)
*B29C 45/00* (2006.01)
*B29C 44/02* (2006.01)

(52) U.S. Cl.
USPC .............. 264/53; 264/328.1; 264/328.17

(58) Field of Classification Search
None
See application file for complete search history.

(56) References Cited

U.S. PATENT DOCUMENTS

| | | | |
|---|---|---|---|
| 5,158,986 A | | 10/1992 | Cha et al. |
| 6,169,122 B1 * | | 1/2001 | Blizard et al. ............ 521/79 |
| 8,137,600 B2 * | | 3/2012 | Pierick et al. ............ 264/45.1 |
| 2004/0198853 A1 | | 10/2004 | Saito et al. |
| 2004/0212118 A1 | | 10/2004 | Vadala, Jr. et al. |
| 2008/0050576 A1 * | | 2/2008 | Pierick et al. ............ 428/304.4 |
| 2010/0198133 A1 | | 8/2010 | Dougherty, Jr. et al. |
| 2012/0061867 A1 * | | 3/2012 | Dougherty et al. ............ 264/13 |

FOREIGN PATENT DOCUMENTS

| EP | 1205511 A1 | 5/2002 |
|---|---|---|
| EP | 12646472 A1 | 12/2002 |

OTHER PUBLICATIONS

International Search Report and Written Opinion for PCT US2011051030 dated Nov. 29, 2011.

* cited by examiner

*Primary Examiner* — Benjamin Schiffman
(74) *Attorney, Agent, or Firm* — Playtex Products, Inc.

(57) ABSTRACT

In a method of microcellular injection molding, a polymer and a supercritical fluid are processed. A condition of processing the polymer and/or the supercritical fluid is adjusted to control a weight of a plastic part and/or a surface characteristic of a plastic part produced. In another method of producing a plastic part using microcellular injection molding, a polymer is heated and melted and a supercritical fluid is added thereto. The resulting mix is a single-phase polymer-gas solution comprising the polymer and the supercritical fluid. The polymer and/or the supercritical fluid are adjusted to control the weight of the plastic part and/or a surface characteristic of the plastic part. Once adjusted, the melted polymer with the supercritical fluid is injected into a mold. Upon injecting the melted polymer and supercritical fluid, a pressure drop causes the supercritical fluid to nucleate in the melted polymer, thereby causing nucleation of bubbles.

28 Claims, 10 Drawing Sheets

METHODS FOR MICROCELLULAR INJECTION MOLDING

TECHNICAL FIELD

The present invention is directed to injection molding and, more particularly, to methods of using microcellular injection molding techniques in manufacturing personal and consumer care products and packaging.

BACKGROUND

Many personal and consumer products and packages are made of plastic. Most plastics are thermoplastics. Thermoplastics, when in solid form, melt and flow when they are heated and re-solidify upon cooling. This process is repeatable. On the other hand, some plastics are thermosetting, which means they react or crosslink under heat and pressure and set to form solids. The term "crosslink" means the attachment of two chains of polymer molecules by a bridge formed by an element, a group, or a compound that joins a carbon atom on one chain to a carbon atom on another chain by primary chemical bonds to form a crosslinking network.

Methods for processing either type of plastic, especially thermoplastics, to make personal and consumer products and packaging include injection molding, blow molding, extrusion, thermoforming, and the like. While such processes have been widely used, there are still drawbacks with these present-day processes and with the products made by these processes.

For instance, processing variables have a direct effect on the surface quality and aesthetics of plastic parts manufactured from microcellular foam using injection molding techniques. Gases, for example, are often introduced into the plastic during processing and can detract from the ability to form smooth surfaces in the finished product by contributing to the formation of undesirable surface features. Such undesirable surface features typically occur as swirling patterns or a gritty texture, which place limitations on the manufacturing of the parts. In particular, swirls and gritty textures produce a rough surface quality that not only results in an unappealing finished product, but often undesirably affect the ability to mold parts having thin-walls or similar geometries and/or parts through which channels or the like are desired.

The desire for obtaining a smooth surface, therefore, is one factor in the selection of a molding process using microcellular foam to produce a molded part. There are two major mechanisms that contribute to the formation of rough surfaces in microcellular foam: 1) the gas escapes from the microcellular foam when the microcellular foam is in melt form, or bubbles from the melt overgrow and break; and 2) the bubbles from the melt are sheared in the interface between the mold wall and melt. In either mechanism, the surface of the part produced is compromised via the formation of a defect on the boundary surface thereof.

Moreover, surface roughness is related to the mold filling pattern, and injection processing conditions may influence surface quality significantly. Three different methods exist to smooth the surface for microcellular foamed parts: 1) use of co-injection or gas counter pressure molding processes; 2) use of hot mold surfaces or coated mold surfaces; and 3) surface improvements resulting from processing, mold, material or part design.

Because the current use of microcellular injection molding technology to produce molded parts is less than adequate for some products, measures have been taken to improve surface part quality. These measures include the use of hot, coated surfaces; the use of gas counter-pressure; special developments with regard to the grade of resin used; and/or co-injection. Such measures can be costly, time-consuming, and/or require complicated mold redesigns and operation.

SUMMARY

In one aspect, the present invention resides in a method of microcellular injection molding. In such a method, a polymer and a supercritical fluid (gas) are processed, for example, by being combined in a suitable mixing apparatus. A condition of processing the polymer and/or the supercritical fluid is adjusted to control the weight of a plastic part and/or a surface characteristic of a plastic part produced.

In another aspect, the present invention resides in a method of producing a plastic part using microcellular injection molding. In this method, a polymer is heated and melted and a supercritical fluid is added thereto. The resulting mix is a single-phase polymer-gas solution comprised of the polymer and the supercritical fluid. The polymer and/or the supercritical fluid are adjusted to control the weight of the plastic part and/or a surface characteristic of the plastic part. Once adjusted, the melted polymer with the supercritical fluid therein is injected into a mold. Upon injecting the melted polymer with the supercritical fluid into the mold, a pressure drop causes the supercritical fluid to nucleate in the melted polymer, thereby causing nucleation of bubbles in the polymer.

In another aspect, the present invention resides in a method of molding a tampon applicator. In doing so, a polymer comprising a low density polyethylene (or similar resin) is heated and melted, and nitrogen, carbon dioxide, or a similar gas or supercritical fluid (SCF) is added to the resulting melt to produce a single-phase polymer-gas solution. At least one of the polymer and the SCF is adjusted to control either or both the weight of the tampon applicator' produced and/or a surface characteristic of the tampon applicator produced. The melted polymer with the SCF therein is injected into a mold, and the mold is cooled. Injecting the melted polymer with the SCF therein into the mold causes a pressure drop that causes cells of the nitrogen to nucleate in the melted polymer, thereby causing nucleation of bubbles in the polymer.

In the processes described herein, the surface quality of injection-molded plastic parts is improved over that of the microcellular foam injection molding techniques of the prior art. Such improvements largely result from the amounts of supercritical fluid (hereinafter "SCF") used (lowering the SCF concentrations relative to amounts used in microcellular foam injection molding techniques of the prior art), which allows for the control of the bubble nucleation rate. In lowering the SCF concentrations used in the techniques of the present invention, the incidences of swirling patterns and gritty texture are reduced or eliminated.

Methods employing reduced concentrations of SCF, such as those described herein, can be implemented in existing molds and provide improvements over other methods of reducing swirling patterns and gritty texture. In fact, the surface appearance for the produced parts exhibiting a weight reduction of about 7% with low SCF concentrations is more desirable than that observed for solid (i.e. unfoamed) parts in that surface irregularities are minimal and there are no observable swirling patterns.

Moreover, with the processes and techniques of the present invention, desirable dimensional stability is obtained in the parts produced, molded-in stresses are reduced, and various mechanical properties (e.g. modulus) are lower as compared to parts produced by methods of the prior art.

Additionally, the implementation of microcellular injection molding techniques using low SCF concentration and low flow rate (and additional process changes) is likely to provide still greater benefits in injection molding processing and in molded part quality. Specifically, material and process changes that facilitate synergistic effects to further improve molding and/or molded parts as compared to techniques of the prior art include the use of slightly different resin grades (e.g., those having higher modulus values and less tendency to crystallize) to improve mechanical properties and/or to modify gas-polymer solubility; the use of slip agents and/or internal lubricants to slightly lower the melt viscosity, to retard crystallization rates, to reduce friction, and thus create a slip condition at the polymer melt-mold wall surface (enabling plug flow over fountain flow) and/or to modify gas-polymer solubility; and the use of insulating materials on the wall or the use of hot or coated surfaces. Mini-valve gates for use in hot runner injection molded systems may also be incorporated to prevent plastic "drooling."

Still other benefits can be derived from compositional modifications of either the SCF, the resin, and/or resin additives to provide (1) desired solubility profiles (which influence nucleation rate); (2) changes in melt temperature that will allow the melt to fill the cavity but also to lower the bubble nucleation rate and thus improve surface quality; and/or (3) the use of "core-back" technology, in which, once the foamed resin fills the mold, the volume of the mold is increased, causing the foam to expand, resulting in stiffer parts with low density, good rigidity, additional weight reduction, and good strength, with adequate surface quality.

DETAILED DESCRIPTION

Figure 1:
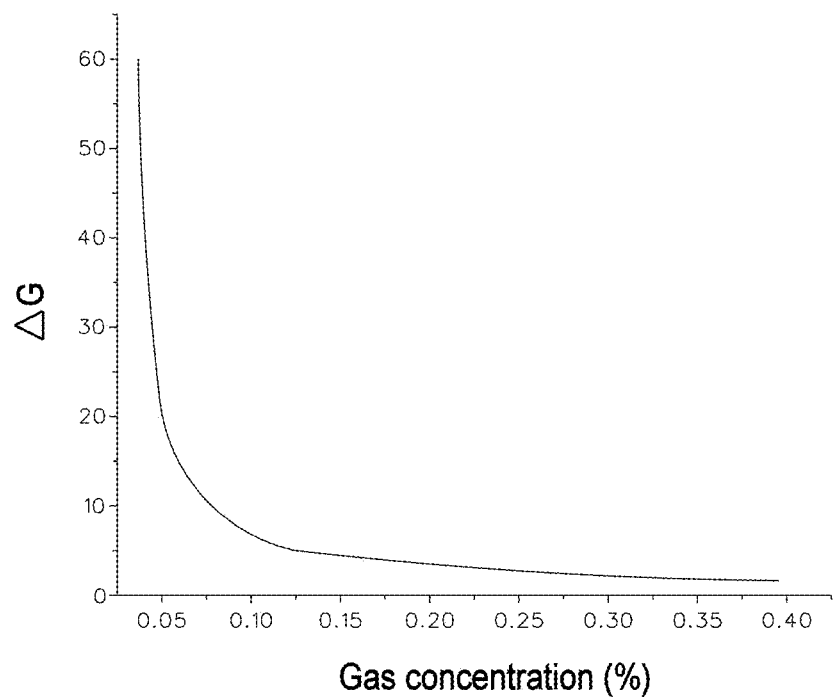
FIG. 1 is a graphical representation of a theoretical plot showing the relationship of activation energy relative to the concentration of supercritical fluid in a polymer.

In the microcellular foam injection molding processes of the present invention, various process parameters are manipulated to achieve improvements (as compared to processes of the prior art) in surface quality and aesthetic characteristics of molded plastic-based products, particularly by reducing the occurrences of swirling patterns and gritty textures. Such manipulation of process parameters includes the reducing of concentrations of supercritical fluids (SCF), as compared to processes and methods of the prior art. In doing so, plastic usage and the overall cost of the products will still be reduced, but surface and mechanical properties are improved. Molded plastic-based products produced by the processes and methods of the present invention include, but are not limited to, consumer and personal care items such as razors, infant care products, feminine hygiene products, and associated packagings thereof. The processes of the present invention are particularly applicable to tampon applicators. Thus, the processes described herein are supported by theoretical considerations that save money and resources while providing suitable surface qualities and aesthetic properties for plastic molded parts.

Without being restricted to any particular theory, the present invention involves the practical applications of nucleation of bubbles in polymeric foam. Process and compositional parameters are derived from theory and have been changed to affect bubble nucleation rate and, in turn, surface quality.

In polymeric foam, nucleation refers to the initial stage of the formation of gas bubbles in a polymer-gas solution. For nucleation to occur, gas bubbles formed by the SCF overcome the free energy barrier (barrier to bubble formation) before the bubbles can grow to macroscopic size. According to classical nucleation theories, the nucleation rate is controlled by the macroscopic properties of the polymer and the gas. Such properties include, but are not limited to, solubility, diffusivity, surface tension, gas concentration, temperature, and the degree of supersaturation of the polymer.

One equation for modeling the nucleation rate of gas in polymeric foam was developed and proved experimentally using a microcellular batch process (a high pressure vessel method). This equation (hereinafter Equation 1) applies to the nucleation rate of gas in microcellular foam and is derived from classical nucleation theory:

$$N = fC\exp\left(-\frac{\Delta G^*}{kT}\right) \quad (1)$$

where N is the number of bubbles generated, f is the frequency of atomic molecular lattice vibrations, C is the concentration of gas molecules, k is the Boltzmann constant, T is the absolute temperature, and $\Delta G^*$ is the activation energy barrier for nucleating bubbles.

The nucleation rate of polymeric foam may be either homogeneous or heterogeneous. The activation energy for homogeneous nucleation is given by Equation 2:

$$\Delta G_{hom} = \frac{16\pi\gamma^3}{3\Delta P^2} \quad (2)$$

where $\gamma$ is the surface (interfacial) energy of the polymer and $\Delta P$ is assumed to be the gas saturation pressure. More precisely, as shown in Equation 3, $$\Delta P = P_r' - P_r \quad (3)$$

In Equation 3, $P_r'$ is the pressure that is exerted on a pressure vessel, and $P_r$ is the pressure of the supersaturated vapor on the sample in such a way that $\Delta P$ is the pressure difference between the pressure that is applied to the sample and the pressure of the supersaturated vapor on the sample.

The activation energy for heterogeneous nucleation is affected by a geometric factor that is related to the contact angle between the polymer and a droplet of fluid. This geometric factor is multiplied by the expression given in Equation 2 above to compute the activation energy for heterogeneous nucleation.

In a microcellular batch process, the foregoing theory has been confirmed by experiment. While nucleation theory can be generally applied to microcellular injection molding, it is modified when the amount of saturated gas is low. With low levels of saturated gas, the degree of supersaturation of the polymer becomes a factor in predicting the nucleation rate. To estimate $\Delta P$ and to consider the degree of supersaturation, another activation energy equation for nucleation can be derived by starting with the Laplace/Kelvin equation for capillary pressure (Equation 4):

$$\Delta P = P'_r - P_r = \frac{2\gamma}{r} \tag{4}$$

where r is the radius of a characteristic droplet. The Thomson equation (Equation 5) is also applicable:

$$RT \ln \frac{P_r}{P_\infty} = \frac{2\gamma M}{r\rho} \tag{5}$$

Here $P_\infty$ is the pressure of the saturated vapor (i.e. the equilibrium pressure), R is the universal gas constant, M is the molar mass, and $\rho$ is the density.

By combining equations, Equation 6 is obtained:

$$\Delta P = kT\rho_l \ln S \tag{6}$$

where $\rho_l$ is the molecular density of the bulk fluid and S is the degree of supersaturation.

By substituting Equation 6 into Equation 2, the activation energy equation for nucleation in the microcellular injection molding process is obtained as Equation 7:

$$\Delta G_{hom} = \frac{16\pi\gamma^3}{3(kT\rho_l \ln S)^2} \tag{7}$$

Hence, the activation energy for nucleation is inversely proportional to the square of the degree of supersaturation of the polymer. Referring to FIG. 1, the relationship of the activation energy relative to the concentration of the gas is nonlinear. Supersaturation of the polymer is kept low by maintaining the SCF concentration at a low level (see FIG. 1), which in turn keeps the activation energy sufficiently high. The low SCF concentration allows for a sizable, steady, but slow bubble nucleation rate to be maintained, thereby preventing an excess of sheared or deformed bubbles at the surface. The actual concentration of the SCF concentration for preventing an excess of sheared or deformed bubbles at the surface and maintaining good surface quality depends on a variety of factors related to the polymer, the configuration of the part being molded (e.g., the thickness), and the molding process parameters (e.g., temperatures and pressures).

In one microcellular injection molding process of the present invention, the polymer-gas solution is transformed to a metastable supersaturated solution as it is injected into a mold cavity, since the amount of SCF that can be dissolved in the polymer under atmospheric pressure is less than the amount of SCF actually dissolved in the polymer melt under the conditions of injection. In this process, the degree of supersaturation can be expressed as (Equation 8):

$$S = \frac{\dot{m}t + D_P}{S_{T,P}} \tag{8}$$

where $\dot{m}$ is the mass flow rate of the gas, t is the gas dosing injection time, $D_P$ is the initial pressure pulse, and $S_{T,P}$ is the solubility of gas at polymer at atmospheric pressure and at the polymer melt temperature. The numerator represents the total mass of SCF added.

When the dosage level is very small, a transient gas pressure pulse at the beginning of the dosing process becomes a non-negligible part of the total dosage, and an accurate determination of the mass added to the system includes both the transient pressure pulse contribution $D_P$ and the steady-state flow contribution. By means of practices such as mass pulse dosing to estimate the pressure pulse contribution from the pressures and material properties of the SCF, as well as automatic delivery pressure control, a total dosing parameter $D_T = \dot{m}t + D_p$ can be accurately and precisely determined.

The solubility of the SCF in the polymer follows an Arrhenius-type expression with regard to temperature, as indicated in Equation 9:

$$S_{T,P} = S_{STP} \exp\left(\frac{-\Delta H}{R}\left(\frac{1}{T_{melt}} - \frac{1}{T_{STP}}\right)\right) \tag{9}$$

where $S_{STP}$ is the solubility of the SCF in the polymer at standard temperature $T_{STP}$ and pressure conditions (298 K and 1 atm). The measurable $\Delta H$ is the molar heat of sorption, R is the universal gas constant, and $T_{melt}$ is the polymer melt temperature. Thus, the degree of supersaturation is given in Equation 10 by $$S = \frac{\dot{m}t + D_P}{S_{STP}} \exp\left(\frac{\Delta H}{R}\left(\frac{1}{T_{melt}} - \frac{1}{T_{STP}}\right)\right) \tag{10}$$

In Equation 10, both $\dot{m}$ and t can be controlled by a SCF supply/control system. The heat of sorption of various polymer-gas systems at standard temperature can be measured or estimated. Solubility data is available in reference literature for many systems of commercial interest. The influence of crystallinity on solubility is also available in the reference literature. Alternatively, the solubilities could be experimentally determined as needed. Ideally, in order to calculate the degree of supersaturation for a polymer-gas solution in a microcellular injection molding process, the solubility of the SCF in the polymer at standard temperature and pressure should be measured. However, the present invention is not so limited.

The processing parameters or material based quantities listed in the above paragraphs are $T_{melt}$, $S_{STP}$, $\Delta H$, $S_{T,P}$, $\dot{m}$, and t. Particularly $\dot{m}$ and t can be manipulated as desired, by either adjustments to process conditions or adjustments to the materials employed, in order to achieve a sufficiently low supersaturation value S. The activation energy barrier for nucleation (Equation 7) and the nucleation rate (Equation 1) can then be calculated. Accordingly, a desired nucleation rate can be determined from the equations above. This value is one that allows for both economical part weight reduction and good surface quality and aesthetics.

The present invention utilizes the application of the above theory to adjust processing conditions—most particularly the SCF quantity as determined from ṁ and t, to achieve both part weight reduction and desirable surface quality by slowing down the nucleation rate. This provides an inexpensive, uncomplicated solution to the problem of obtaining both reasonable part weight reduction as well as desirable surface quality with microcellular injection molding processes. Other properties of the parts produced, such as dimensional stability, mechanical properties, and coefficient of friction, can also be measured and controlled.

In the present invention, microcellular injection molding is carried out in which the molding is achieved with less SCF as compared to molding processes of the prior art; i.e., in which the SCF injection time is reduced from 2 seconds to about 0.5 seconds to about 0.9 seconds and more preferably to about 0.65-0.75 seconds; the SCF pressure is reduced from 5-10 bar to about 0.5-2.5 bar and more preferably about 1-2 bar; and the SCF flow rate is reduced from the 0.08-0.11 kg/hr to about 0.04-0.06 kg/hr and more preferably to about 0.045-0.055 kg/hr. With these reductions, parts with an acceptable surface finish are obtained. The resulting weight reduction of parts produced is about 7%.

EXAMPLE 1

Polymer Formulation

A resin of low density polyethylene (LDPE) (MARLEX KN226, available from Chevron-Phillips Chemical Company LLC, The Woodlands, Tex.) was mixed together with a green LDPE-based masterbatch formulation to produce the following mixture, hereinafter "the LDPE resin mix":

LDPE 98.493%
Mica 0.606%
$TiO_2$ 0.516%
Erucamide 0.25%
Ethylene bis-stearamide 0.125%
Colorant<0.01%

(The latter five components, together with a small percentage of the LDPE, comprise the green color concentrate described in the Examples below. Addition of color concentrate is optional and thus may be omitted from the formulations.)

As another polymer formulation, oleamide of 1 wt % was added into the LDPE resin. Oleamide was used as an anti-nucleating agent since oleamide could block the fluxes of gas molecules throughout the polymer matrix resulting in a low degree of supersaturation.

LDPE 97.493%
Oleamide 1%
Mica 0.606%
$TiO_2$ 0.516%
Erucamide 0.25%
Ethylene bis-stearamide 0.125%
Colorant<0.01%

Similarly, 1.5 wt % of EBS was added into the LDPE resin.
LDPE 96.993%
Ethylene bis-stearamide 1.5%
Mica 0.606%
$TiO_2$ 0.516%
Erucamide 0.25%
Colorant<0.01%

EXAMPLE 2

Plastic Part Molding Experiment

The LDPE resin mix was used in an injection molding trial to make test specimen parts using the following experimental setup:

Injection Molding Machine: Arburg 320S Allrounder 55 ton (available from Arburg, Inc., Newington, Conn.)
SCF Unit (available from Trexel, Inc., Woburn Mass.)
Supercritical Fluid: Nitrogen Two types of experiments were performed, namely (1) tensile bar experiments and (2) experiments with small test molds for tampon applicator barrels (commercially available "super" size tampons). Table 1 provides the molding conditions used in the tensile bar experiments.

TABLE 1

Process conditions for tensile bar molding examples.

| Description | Tensile Test Bar Solid |
| --- | --- |
| Molding Machine | Arburg 320S |
| Material | LDPE (KN226) + 5% Green Colorant |
| Mold | ASTM D638 Tensile Test Bar |
| Runner System | Cold Runner |
| Total Cycle Time (second) | 55 |
| Screw Diameter (mm) | 25 |
| Mold Cooling Temperature (° C.) | 25 |
| Nozzle Temperature (° C.) | 216 |
| Zone 4 (° C.) | 221 |
| Zone 3 (° C.) | 221 |
| Zone 2 (° C.) | 218 |
| Zone 1 (° C.) | 215 |
| Cooling Time (sec) | 40 |

Figure 2:
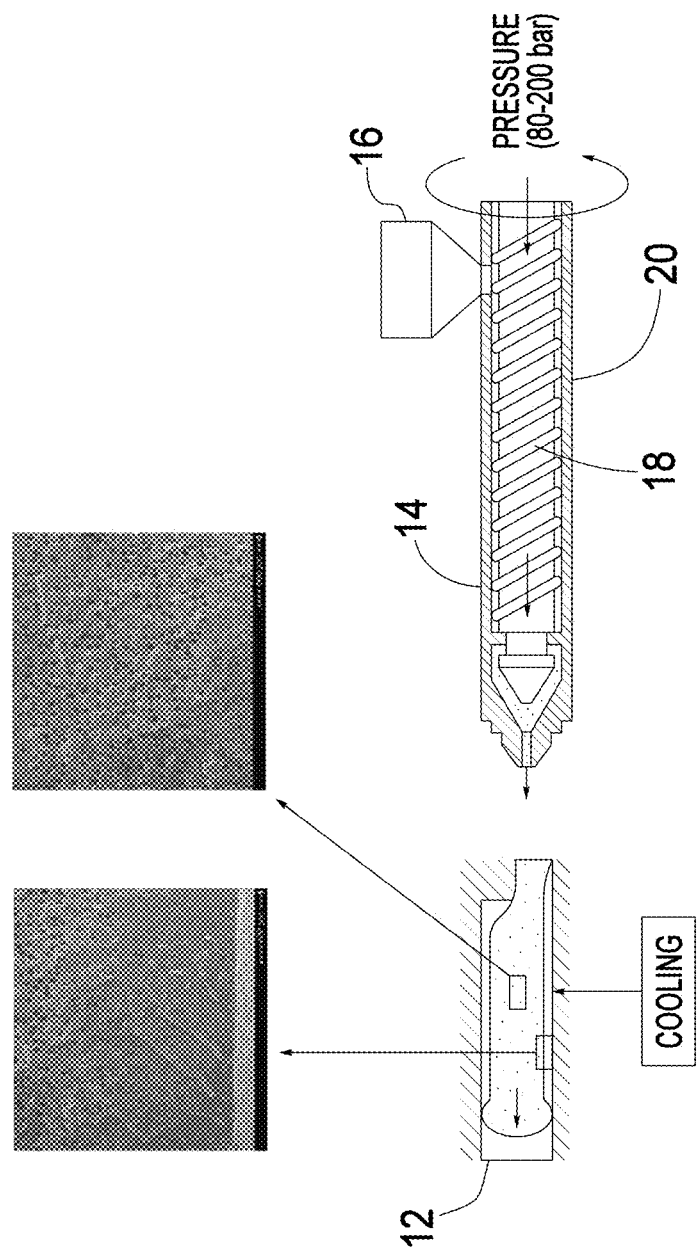
FIG. 2 is a schematic representation of an apparatus used in a process of mixing a polymer and a supercritical fluid.

Referring to FIG. 2, an apparatus for carrying out the microcellular injection molding process of the present invention is schematically shown designated generally by the reference numeral 10 and is hereafter referred to as "apparatus 10." Apparatus 10, which facilitates the mixing of the LDPE resin mix (and optional colorant) with SCF, includes a screw conveying section 18, a hopper 16 through which the LDPE resin mix is added to this conveying section, and an injection molding portion 12. The screw conveying section 18, which comprises a plasticizing screw to transport the LDPE resin mix from the introduction thereof through the hopper 16 to the injection molding portion 20, also includes a feed system 14 for the supercritical fluid addition. The back pressure provided between the screw conveying section 18 and the injection molding portion 12 is about 10 bar to about 200 bar, more preferably 30 bar to 100 bar. The LDPE resin mix is heated as it moves from the hopper 16 through the conveying section 18 using primarily the mechanical energy from the rotation of the plasticizing screw and any suitable heating means (e.g., heat from shear or heat from an electrical source) to produce the molten LDPE resin mix. When the SCF is added via the feed system 14, the resulting melt becomes a single-phase polymer-gas solution. The single-phase polymer-gas solution comprising the SCF is then injected into a mold via a suitable system of runners and gates. The rapid pressure drop as the solution leaves the conveying section 18 leads to the formation of nuclei and the microcellular injection molded parts having about as many as about $10^6$ to about $10^9$ pores per cubic centimeter of material. Such microcellular plastics made by this process have solid skin layers and foamed core parts.

TABLE 2

Tensile bar injection molding conditions.

| Sample | C1 | E1 | E2 | E3 | C2 |
|---|---|---|---|---|---|
| Description | Tensile Test Bar Solid | Tensile Test Bar (micro-cellular) (8%) | Tensile Test Bar (micro-cellular) (8%) | Tensile Test Bar (micro-cellular) (8%) | Tensile Test Bar (micro-cellular) (8%) |
| SCF Dosage Start ($cm^3$) | — | 8 | 8 | 8 | 8 |
| SCF Dosage Time (sec) | — | 0.7 | 0.75 | 0.8 | 1.5 |
| SCF Flow Rate (kg/hr) | — | 0.05 | 0.06 | 0.07 | 0.11 |
| SCF Weight vs. Part Weight (weight %) | — | 0.068 | 0.088 | 0.110 | 0.323 |
| SCF Injection Pressure (bar) | — | 130 | 130 | 130 | 130 |
| Shot Volume ($cm^3$) | 20.4 | 19.5 | 19.5 | 19.5 | 19.5 |
| Switchover ($cm^3$) | 1.1 | 1.1 | 1.1 | 1.1 | 1.1 |
| Injection Speed ($cm^3$/sec) | 15 | 80 | 80 | 80 | 80 |
| Injection Pressure (bar) | 800 | 1200 | 1200 | 1200 | 1200 |
| Pack Pressure (bar) | 1800 | — | — | — | — |
| Pack Time (sec) | 8 | — | — | — | — |
| Circumference Speed (m/min) | 12 | 15 | 15 | 15 | 15 |
| Cooling Temp (deg C.) | 38 | 25 | 25 | 25 | 25 |
| Back Pressure (bar) | 10 | 60 | 60 | 60 | 60 |

Table 2 provides the various operating conditions (i.e., dosage times, supercritical fluid flow rates, etc.) for the tensile bar experiments that exemplify this invention. Note that there are two comparative samples (C1 and C2) and three samples (E1-E3) that correspond to the present invention.

TABLE 3

Results for examples of the present invention versus comparative examples.

| Sample | C1 | E1 | E2 | E3 | C2 |
|---|---|---|---|---|---|
| Pan Weight (g) | 7.10 | 6.53 | 6.54 | 6.55 | 6.56 |
| Surface | No swirl marks | No swirl marks | No swirl marks | No swirl marks | Swirl marks |
| Shrinkage in Thickness Direction (%) | 0.32 | 0.8 | 0.56 | 0.38 | −1.52 |
| Shrinkage in Width Direction (%) | 1 | 1.64 | 1.5 | 1.16 | −0.06 |
| Shrinkage in Length Direction (%) | 1.17 | 1.33 | 1.25 | 1.19 | 0.763 |

Table 3 provides a summary of various results. Besides the weight reduction and surface quality ratings, changes in thickness, width, and length directions were measured for the samples of Table 2 using calipers. About ten measurements per sample were checked for dimensional stability. Table 3 reports the average shrinkage in these dimensions. As can be seen, the comparative sample C1 (solid, non-microcellular) exhibits no weight reduction. Comparative sample C2 (high supercritical fluid flow) exhibits weight reduction, but also exhibits poor surface quality and high shrinkage in the thickness direction. On the other hand, samples E1-E3 exhibit reasonable weight reduction, good surface quality, and good dimensional stability.

Figure 3A:
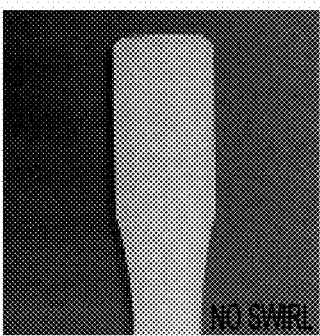
FIG. 3A is a photograph of a first molded tensile bar.
Figure 3B:
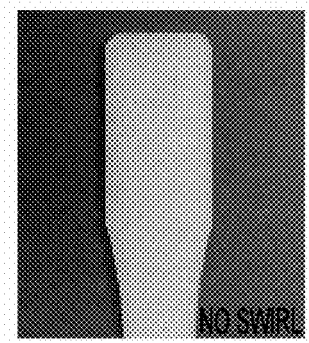
FIG. 3B is a photograph of a second molded tensile bar.
Figure 3C:
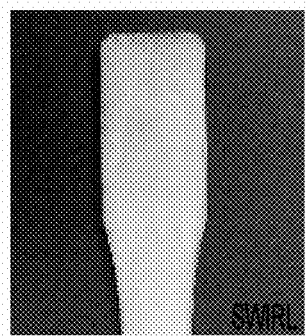
FIG. 3C is a photograph of a third molded tensile bar.

Referring now to FIGS. 3A, 3B, and 3C, microcellular plastic parts (in the forms of tensile bars) were molded using operating conditions similar to those for C1 (solid, displayed on the right) and the experimental examples E1-E4, except that the colorant was omitted from these molding formulation examples so that surfaces could be more easily observed. In FIG. 3A, a first tensile bar was molded with SCF being added at a rate of 0.05 kg/hr for 0.7 seconds. One SCF injection was made for every two shots of the LDPE resin mix for a sample having 0.1 wt. % gas. The surface of the first tensile bar exhibited no swirl in the texture. In FIG. 3B, a second tensile bar was molded with SCF being added at a rate of 0.05 to 0.07 kg/hr for 0.7 to 0.8 seconds. SCF injection was made for a sample having about 0.1 to 0.2 wt. % gas. The surface of the second tensile bar exhibited no swirl in the texture. In FIG. 3C, a third tensile bar was molded with SCF being added at a rate of 0.11 kg/hr for 1.5 seconds. One SCF injection was made for every two shots of the LDPE resin mix for a sample having about 0.2 wt. % gas. As FIG. 3C shows, at this higher SCF level, some swirl was observed on the surface of this third tensile bar.

Figure 4:
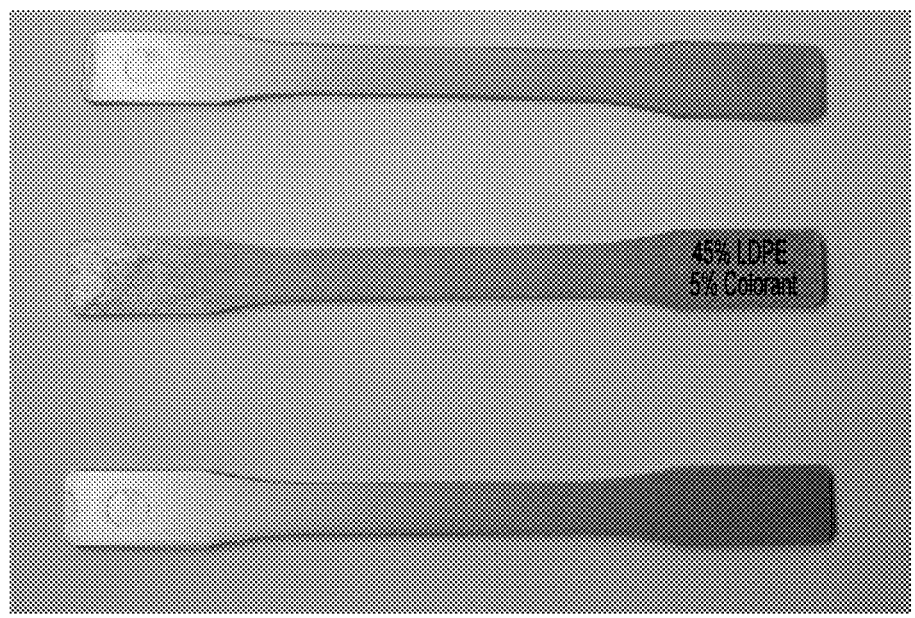
FIG. 4 is a photograph of three molded tensile bars.

Referring now to FIG. 4, a similar comparison was made using the green colorant. Injection molded parts from samples C1, C2, and E1 show that the low SCF-concentration part exhibits the most desired overall surface quality and aesthetics, with concomitant part weight reduction.

Figure 5:
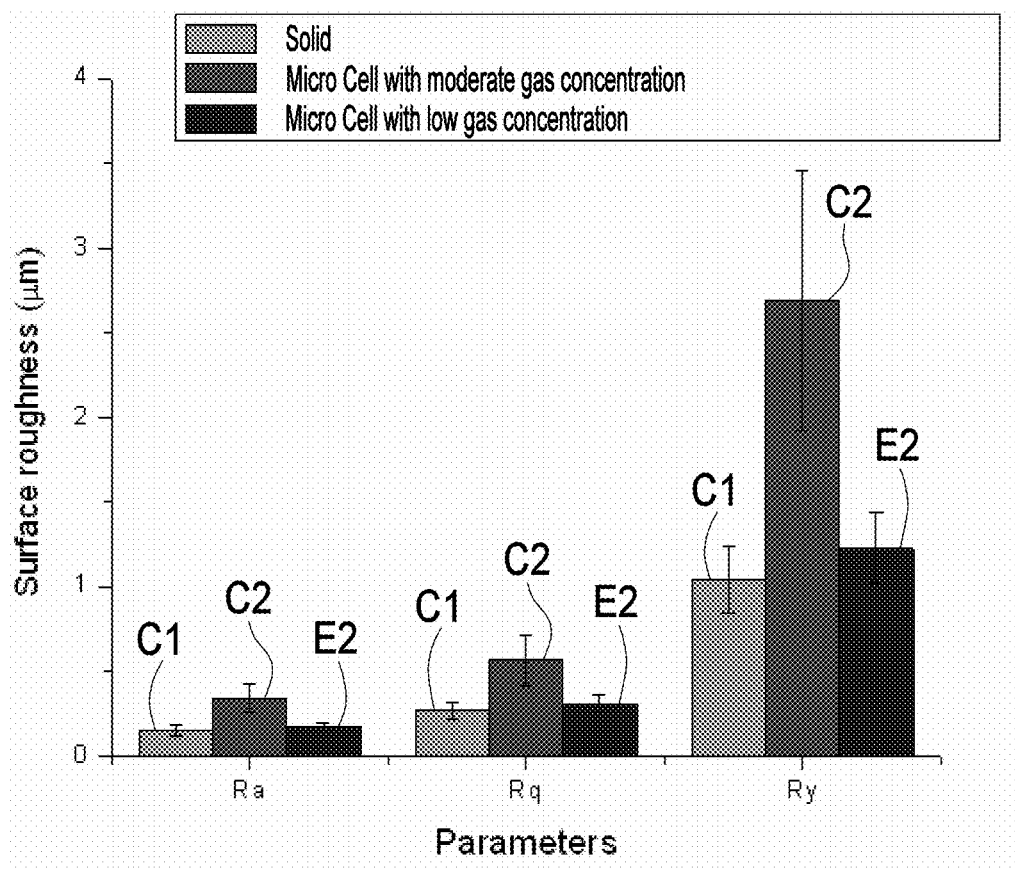
FIG. 5 is a graphical representation of surface roughness parameters for various molded parts.

In this comparison, surface quality is qualitative, but surface roughness can be quantified. Referring now to FIG. 5, a SURFANALYZER 4000, available from Mahr Federal Inc. (Providence R.I.), was used to quantify the surface roughness. As shown in FIG. 5, the low SCF sample E2 exhibits surface roughness by all three measures that are statistically comparable to those for the solid injection-molded part (C1). Sample C2 has a moderately high SCF concentration. Ra is the average roughness, Rq is the root-mean-square of roughness, and Ry is the maximum roughness. Both mean values and standard deviations for the parameters are provided for all three samples (C1, C2, and E2).

Figure 6C:
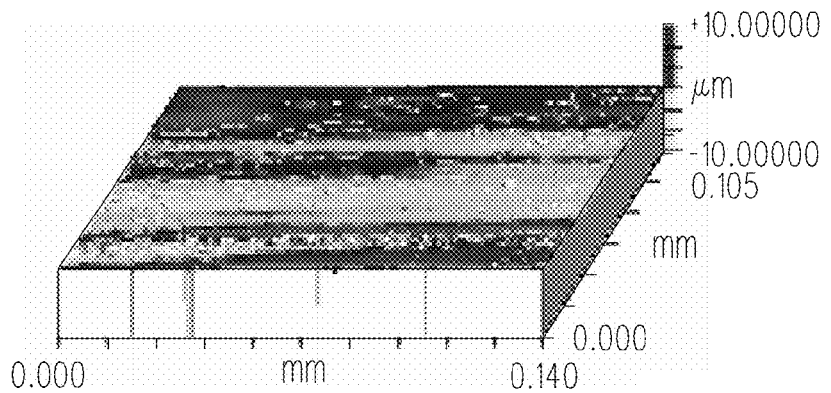
FIG. 6C is a three-dimensional graphical representation of surface roughness of another tensile bar.
Figure 6B:
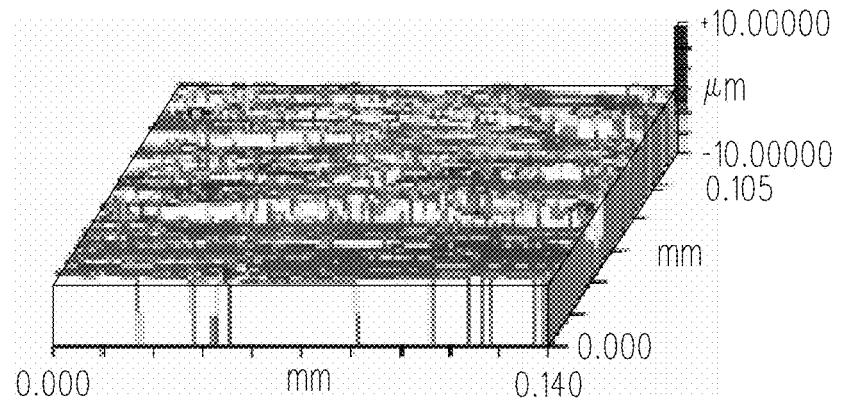
FIG. 6B is a three-dimensional graphical representation of surface roughness of another tensile bar.
Figure 6A:
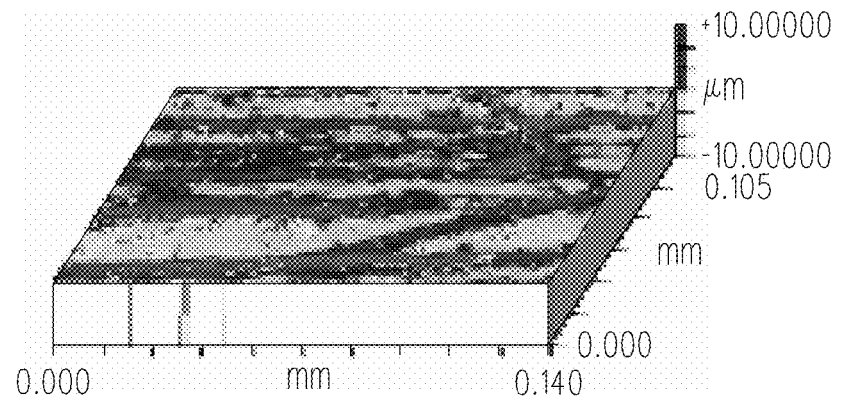
FIG. 6A is a three-dimensional graphical representation of surface roughness of a tensile bar.

As is shown in FIGS. 6A, 6B, and 6C, three-dimensional representations of the surface of the corresponding samples (injection molded tensile bars) are provided. A surface profiler (available from Zygo Corporation, Middlefield, Conn.) shows the improvements to surface by color contour/surface maps for the parts of sample E1 (microcellular plastic injection molded with a low SCF concentration; FIG. 6C). The smoothness, by this measure, rivals that of the solid sample, C1 (conventionally injection molded sample; FIG. 6A). Sample C2 (FIG. 6B) is a microcellular plastic injection molded part with a moderate SCF concentration. High SCF concentrations give rougher surfaces, as noted by the large red color portions.

Based on the foregoing data and Figures, it was concluded that as the concentration of supercritical nitrogen was decreased, surface roughness was reduced and quality was improved, with reasonable (about 7 to 8%) weight reduction. Also, when the supercritical fluid concentration was increased above about 0.2 weight percent, depending on specific processing conditions, swirl marks were evident in the surfaces of the samples. Samples with fairly small and dense bubbles without swirl marks were attained by precisely controlling the exact amount of SCF. Furthermore, samples with low SCF levels exhibit good dimensional stability. Predictions based on nucleation theory have been largely validated by the foregoing experiments.

EXAMPLE 3

Tampon Applicator Experiment

Additional experiments have been performed in which tampon applicator barrels were molded using a four-cavity, hot-runner mold exhibiting significant part complexity. The mold was mechanically mounted and electrically linked both to the Arburg 320S injection molding machine and to the apparatus 10 represented in FIG. 2. A rounded, radiused nozzle was used to inject the plastic. Electrical zone heating for the hot runner manifold was controlled by means of a temperature controller (available from Gammaflux L.P., Sterling, Va.). The mold was cooled using a chilled water system using inlet temperatures of either 10 or 22 degrees C. Except where noted otherwise below, the other parameters and operating conditions were similar to those already described above for Example 2.

Other molding parameters used in the tampon applicator barrel molding are as follows:
  Core pull option set to fire prior to mold open and retracted prior to mold close
  Air actuated part ejection
  Material: LDPE resin mix
  Injection Pressure: 1200 bar
  Overall cycle time: about 30 seconds Table 4 shows the detailed operating conditions for the tampon applicator barrel injection molding experiments. Comparable additional injection molding runs were made. Comparative samples were sample C3 (solid applicator barrel, non-microcellular), while sample C4 provided an additional comparative example (high concentration of SCF, microcellular). In Table 4, ethylene bis-stearamide (EBS) was added for sample E6. Addition of the EBS showed that lubricants, slip agents, and the like that are often added in injection molding formulations either for property enhancements and/or for improved processability and/or improved moldability can also be used with the low SCF level microcellular processes of the present invention.

TABLE 4

Detailed operating conditions.

| Sample | C3 | E5 | C4 | E6 |
|---|---|---|---|---|
| Additive | None | None | None | 1.5% EBS |
| Mold cooling temp. (deg C.) | 15 | 15 | 25 | 25 |
| Nozzle temp (deg C.) | 206 | 206 | 224 | 224 |
| Zone 1-4 Temp profile (deg C.) | 205/208/214/213 | 205/208/214/213 | 216/221/224/224 | 216/221/224/224 |
| SCF Dosage Start (cc) | NA | 4 | 4 | 4 |
| SCF Dosage Time (sec) | NA | 0.21 | 0.2 | 0.13 |
| SCF flow rate (kg/hr) | NA | 0.05 | 0.05 | 0.07 |
| SCF Injection Pressure (bar) | NA | 130 | 135 | 135 |
| Shot Volume (cc) | 10.2 | 9.7 | 9.7 | 9.7 |
| Switchover (cc) | 1 | 1 | 1 | 1 |
| Injection speed (cc/sec) | 20 | 80 | 80 | 80 |
| Pack pressure (bar) | 425 | 100 | 80 | 80 |
| Pack time (sec) | 1.5 | 0.5 | 0.5 | 0.5 |
| Circumference speed (m/min) | 19 | 9 | 9 | 9 |
| Back Pressure (bar) | 5 | 60 | 60 | 60 |
| Cooling time (sec) | 7.5 | 6.5 | 6.5 | 6.5 |
| Manifold temperature (deg C.) | 211 | 211 | 227 | 211 |
| Tip temperature (deg C.) | 232 | 232 | 232 | 232 |
| Suck back | Yes | No | No | No |

Results for the tampon applicator barrel examples are provided in Table 5.

TABLE 5

Results for tampon applicator barrel.

| Sample | C3 | E5 | C4 | E6 | Pooled std. error Estimate |
|---|---|---|---|---|---|
| Part Weight, g | 3.48 | 3.22 | 3.19 | 3.20 | 0.004 |
| Surface | No flow marks | No flow marks | Flow Marks | No Flow Marks | NA |
| Surface Quality Ratings (Semi-quantitative visual and tactile ratings) | Mostly smooth, some scratches | Smooth, slight roughness indicated | Surface very rough, not smooth at all | No scratches, slight roughness | NA |
| Average Surface roughness, microns | 0.718 | 0.917 | 1.011 | 0.888 | 0.05 |
| Average barrel lengths, inches | 3.098 | 3.084 | 3.099 | 3.088 | 0.003 |
| Average finger grip outside diameter, inches | 0.340 | 0.335 | 0.336 | 0.335 | 0.002 |
| Average Kinetic Coefficient Of friction | 0.235 | 0.312 | 0.318 | 0.252 | 0.01 |
| Initial Petal Gap, inches | 0.0558 | 0.0398 | 0.0370 | 0.0341 | 0.006 |

TABLE 5-continued

Results for tampon applicator barrel.

| Sample | C3 | E5 | C4 | E6 | Pooled std. error Estimate |
|---|---|---|---|---|---|
| Final petal gap (after 24 hours at 130 deg F.), inches | 0.0579 | 0.0392 | 0.0560 | 0.0359 | 0.005 |

The dimensions of the various parts in Table 5 were taken using an optical comparator (MONO DYNASCOPE QC 200, available from Vision Engineering Hawk Metronics, Bedford, N.H.).

Tampon applicator barrel surface roughness values were measured for eleven parts per sample using a POCKET SURF II PROFILOMETER (diamond stylus, Ra option) available from Mahr Federal Inc. (Providence, R.I.) and adapted for use with the cylindrical barrel.

Kinetic coefficients of friction were measured in accordance with ASTM D1894 using a mechanical tester (an INSTRON 4411, available from Instron of Canton, Mass.) adapted for use with tampon applicator barrels.

As can be seen in Table 5, barrel surface roughness and surface quality were much improved for samples E5 and E6 as compared to sample C4. Also, there was a notable part weight reduction, thus leading to lower material costs. Additionally, times to pack the mold were shorter, viscosities were lower, and cooling requirements were less, thereby leading to process improvements and cost reductions. Dimensions for the parts were comparable, with differences being associated with making the measurements. Moreover, the dimensions of the parts remained stable over time.

The coefficient of friction was slightly higher with the microcellular-produced parts, although addition of a small amount of additional slip agent (as shown with regard to sample E6) can improve this property as desired. As changes in the LDPE resin mix and/or additives are made, the solubility of SCF in the polymer may change as well.

One property with regard to the manufacture of tampon applicators is petal tip formation and petal tip stability. In a tampon applicator, petals are formed and closed by mechanical pressure and heat. In forming the tampon applicator, the petal tips (of which there are usually four) come together. An optical comparator is used to measure the "circle" defined by the closed tips. Over time, temperature, and humidity, the closed petals can "expand" to "open up," or they may "contract." Values associated with the mechanical properties of the petal tip—and petal tip stability—is improved with the microcellular parts of this invention. The microcellular-produced petals are evidently about 20% "tighter" and remain so. Without being restricted by theory, it is surmised that this may be the result of microcellular parts introducing less overall stresses to the part prior to use by the consumer, thus maintaining part stability in what are somewhat extreme conditions.

Figure 7:
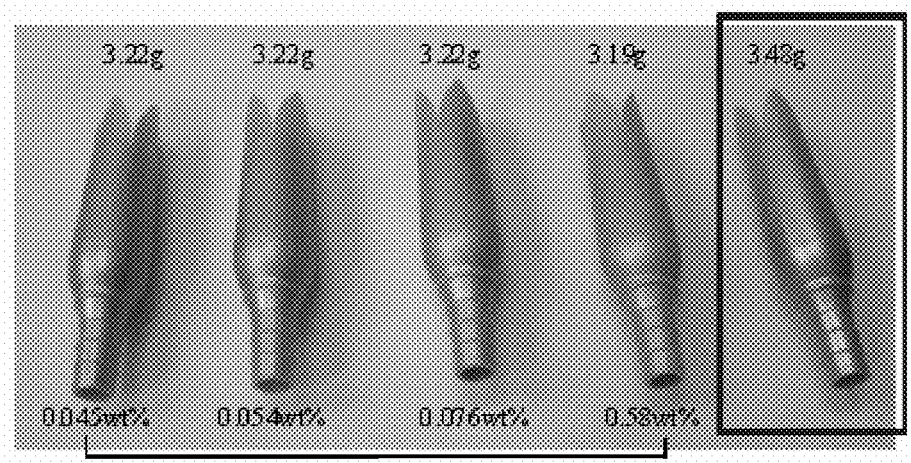
FIG. 7 is a photograph of various injection molded plastic parts.

Referring now to FIG. 7, the surface quality of a tampon applicator barrel is shown as a function of SCF concentration. The surface is improved as the SCF concentration is lowered below 0.2 weight percent. The tampon applicator barrels are injection molded (microcellular) using the LDPE resin mix.

EXAMPLE 4

Infant Care Lid Mold

Figure 8:
FIG. 8 is a perspective view of a molded lid for an infant care product.

Referring now to FIG. 8, a molded lid for a commercially available infant care product is shown. The conditions for molding the lid of example 4 are listed in Table 6.

TABLE 6

Conditions for molding infant care product lid.

| Parameter | Example Example #4, Exp. E7, Infant care lid mold, microcellular Settings |
|---|---|
| Nozzle/Hot Runner Temperature (degrees C.) | 220/220 |
| Additives | 5 wt. % colorant |
| Gas Injection | Mass Pulse Dosing |
| SCF Dosage Start (cm$^3$) | 12 |
| Gas Pressure/Gas Pressure Drop (bar) | 160/25 |
| Approximate Gas Dosage (mg) | 19.7 |
| Shot Volume (cm$^3$) | 29 |
| Injection Speed (cm$^3$/sec) | 80/45/20 |
| Injection Pressure (bar) | 1500 |
| Pack Pressure (bar) (Pack Time(sec)) | 1300 (0.5) |
| Circumference Speed (m/min.) | 15 |
| Back Pressure (bar) | 40 |
| Part Weight (g)/Weight Reduction (%) | 21.3/5.6 |
| Surface Quality | Excellent |

Mass pulse dosing (MPD) control was used to produce the lid. Polypropylene (SR256M from BASF) was used as a material of construction. A small amount of backpressure was applied for 0.5 seconds to reduce shrinkage of the polypropylene in the mold.

This part was made using a relatively low shot volume and an injection speed of 20 cm$^3$/s during filling. The part produced exhibited suitable surface quality.

This and other related microcellular injection molding trials suggest that the maximum weight reduction of microcellular molded parts depends at least to some degree on the geometry of the part. The surface quality and bubble morphology depends on gas amount and injection speed. By slowing injection velocity down during the filling state, uniformly dispersed bubbles in the plastic part can be achieved; this avoids swirl marks on the surface.

Microcellular molded parts were also made, using processing conditions similar to those outlined in Table 6, but with 5% of the green pellet colorant concentrate that had been described in previous examples above. Weight reduction was approximately 5%. The samples produced from repeated injection molding runs showed that the polypropylene with the pearl green colorant did not have swirl marks on the top or bottom. The pellet colorant concentrate enabled substantially swirl-free plastic parts to be produced with a small amount of added super-critical fluid. See FIG. 9 for a comparison of the part made by the microcellular injection molding processes of the present invention to that of a comparably molded, conventional, solid part. Both the top and bottom of the microcellular injection molded part exhibit very good surface quality.

Example 4 shows how versatile the invention is toward providing both weight reduction and desirable surface quality in a very different, complex, molded part.

EXAMPLE 5

Tampon Applicator Barrel Mold

This example shows how microcellular injection molding can be used to achieve suitable part surface quality using a small, two-cavity mold specially designed for microcellular injection molding technology. The mold of this example is a tampon applicator barrel. It is a flared, pin-valve-gated, hot runner mold. Use of such valve gates helps reduce the "plastic drooling" that can result from using supercritical fluid with hot runner systems.

The mold of this example, like that of Example 4, is designed for scale-up for high-speed production molding. The gate location is at the bottom of the part. Proximity switches are used for control and operation of the mold. The water cooling system has been designed for efficient heat transfer. Both hydraulic and pneumatic core pull systems are used.

Table 7 below provides the processing conditions used for Example 5. Conditions used for the solid (comparative) example are provided in the column C5; while those for the microcellular injection molding example are provided in columns E8 and E9.

Figure 9:
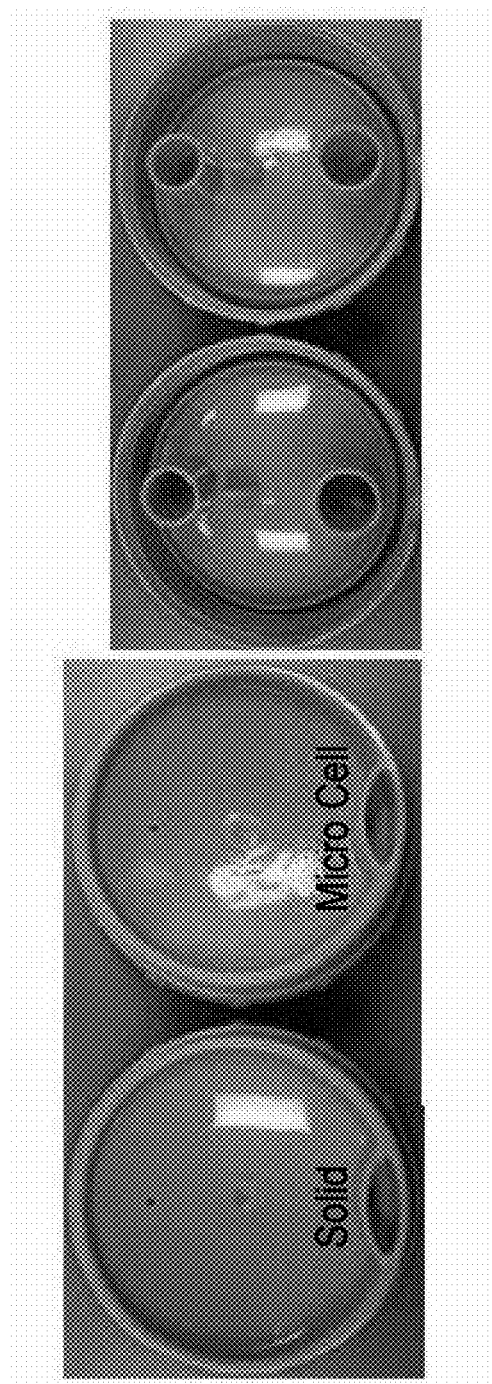
FIG. 9 is a photograph of molded lids for infant care products.
Figure 10:
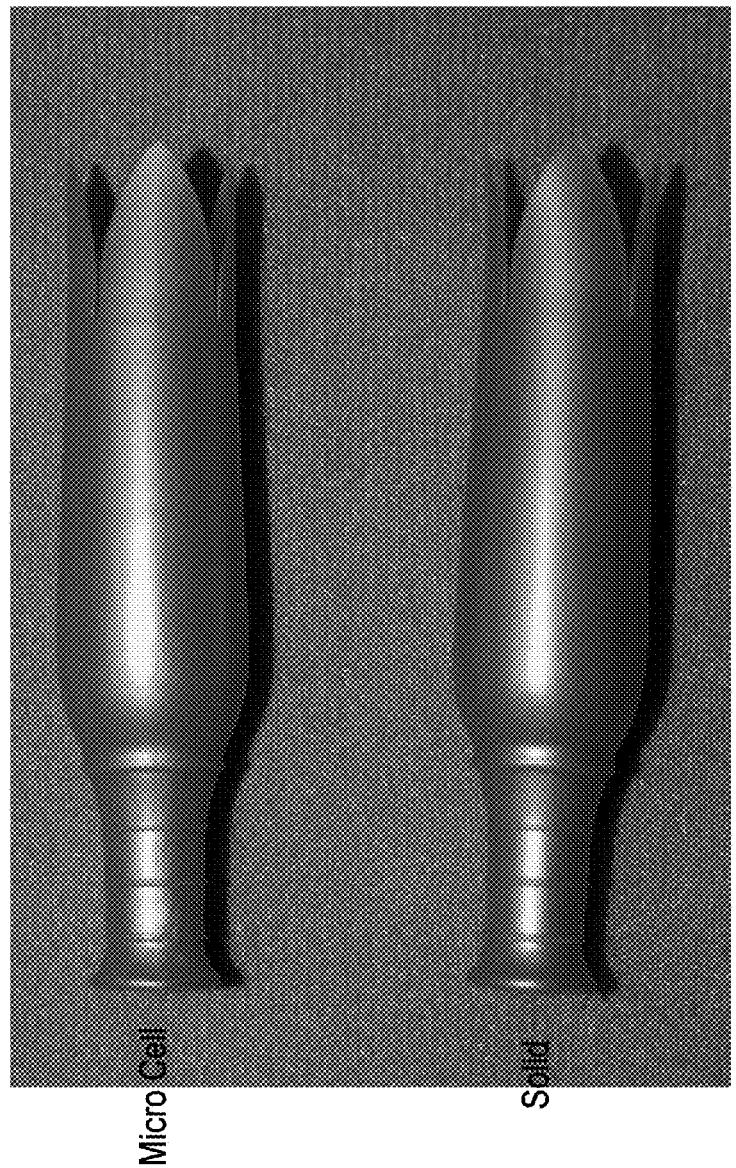
FIG. 10 is a photograph of plastic parts illustrating a comparison of solid molded plastic and microcellular injection molded plastic.

As FIG. 9 shows, the part quality for the microcellular injection molded part in experiment E9 is desirable and is substantially identical to that of the comparably molded solid part, but with 5.9% weight reduction. Also, the microcellular injection molded parts in experiments E8 and E9 have been produced at lower processing/molding temperatures, shorter pack times, and either zero or much lower pack pressures. Furthermore, the processing parameters can be used to produce a tampon applicator having a flared portion at one end, as is shown in FIG. 10. Such process advantages, in addition to the observed weight reduction, can yield significant benefits, with no impact to part quality for a mold designed for efficient microcellular injection molding performance.

TABLE 7

| Molding Conditions | C5, Solid | E8, Microcellular | E9, Microcellular |
|---|---|---|---|
| Material | LDPE (KN226) + 5% Green colorant | LDPE (KN226) + 5% Green colorant | LDPE (KN226) + 5% Green colorant |
| Mold Cooling Temperature (deg C.) | 10 | 25 | 10 |
| Nozzle Temp, deg C. | 216 | 221 | 206 |
| Zone Temps: Zones 1, 2, 3 and 4 | 215/218/224/221 | 205/210/215/218 | 190/195/200/203 |
| SCF Dosage (cc) | N/A | 4.5 | 7 |
| SCF Dosage time (sec) | N/A | 0.35 | 0.25 |
| SCF Pressure Drop (bar) | N/A | 10 | 6 |
| Shot Volume (cc) | 10.2 | 10.2 | 12.5 |
| Back pressure (bar) | 10 | 70 | 60 |
| Injection speed (cc/sec) | 20 | 80/45/1 | 20 |
| Switchover (cc) | 0.8 | 3.5/2.5/1 | 4.4 |
| Pack Pressure (bar) | 425 | N/A | 30-40 |
| Pack time (sec) | 1.5 | 0 | 0.12-0.25 |
| Circumference speed, m/min | 19 | 7 | 7 |
| Hot runner temperature, deg C. | 246 | 224 | 209 |
| Average Part Weight g/(Weight Reduction, %) | 3.194 (N/A) | 3.015 (5.6%) | 3.004 (5.9%) |
| Surface Quality | Very Good | Very Good | Very Good |

Although this invention has been shown and described with respect to the detailed embodiments thereof, it will be understood by those of skill in the art that various changes may be made and equivalents may be substituted for elements thereof without departing from the scope of the invention. In addition, modifications may be made to adapt a particular situation or material to the teachings of the invention without departing from the essential scope thereof. Therefore, it is intended that the invention not be limited to the particular embodiments disclosed in the above detailed description, but that the invention will include all embodiments falling within the scope of the appended claims.

What is claimed is:

1. A method of microcellular injection molding, comprising:
   providing a polymer;
   providing a supercritical fluid to the polymer;
   processing the polymer and the supercritical fluid;
   adjusting at least one condition of processing the polymer and the supercritical fluid to control at least one of a weight of a plastic part produced and a surface characteristic of the plastic part produced from the method of microcellular injection molding; and
   injecting the processed polymer with the supercritical fluid therein into a mold;
   wherein injecting the processed polymer with the supercritical fluid therein into the mold causes a pressure drop of about 0.5 bar to about 2.5 bar that causes the supercritical fluid to nucleate in the processed polymer.

2. The method of claim 1, wherein adjusting at least one condition of processing the polymer and the supercritical fluid comprises determining a nucleation rate of bubbles of the supercritical fluid in the polymer and adjusting a flow of the supercritical fluid provided based on the determined nucleation rate.

3. The method of claim 1, further comprising transforming the processed polymer and supercritical fluid to a metastable supersaturated solution.

4. The method of claim 3, wherein transforming the processed polymer and supercritical fluid comprises injecting the processed polymer and supercritical fluid into a mold cavity.

5. The method of claim 1, wherein providing the supercritical fluid comprises controlling a mass flow rate of the supercritical fluid.

6. The method of claim 5, wherein the supercritical fluid is nitrogen and wherein the plastic part produced is a feminine hygiene product.

7. The method of claim 6, wherein the concentration of the nitrogen is controlled to be about 0.03 wt. % to about 1 wt. %.

8. The method of claim 6, wherein the concentration of the nitrogen is controlled to be about 0.08 wt. % to about 0.25 wt. %.

9. The method of claim 5, wherein the supercritical fluid is carbon dioxide and wherein the plastic part produced is a feminine hygiene product.

10. The method of claim 9, wherein the concentration of the carbon dioxide is controlled to be about 0.3 wt. % to about 3 wt. %.

11. The method of claim 9, wherein the concentration of the carbon dioxide is controlled to be about 0.5 wt. % to about 2 wt. %.

12. The method of claim 1, wherein the supercritical fluid is provided at a pressure of about 10 bar to about 300 bar.

13. The method of claim 1, wherein the supercritical fluid is provided at a pressure of about 70 bar to about 150 bar.

14. A method of producing a plastic part using microcellular injection molding, comprising:

providing a polymer;

heating the polymer to melt the polymer;

adding a supercritical fluid to the melted polymer to produce a single-phase polymer-gas solution;

adjusting at least one of the polymer and the supercritical fluid to control at least one of a weight of the plastic part and a surface characteristic of the plastic part; and injecting the melted polymer with the supercritical fluid therein into a mold;

wherein injecting the melted polymer with the supercritical fluid therein into the mold causes a pressure drop of about 0.5 bar to about 2.5 bar that causes the supercritical fluid to nucleate in the melted polymer.

15. The method of claim 14, wherein the supercritical fluid is nitrogen and wherein adjusting at least one of the polymer and the supercritical fluid comprises adjusting the concentration of the supercritical fluid added to the melted polymer to be about 0.03 wt. % to about 1 wt. %.

16. The method of claim 14, wherein the supercritical fluid is nitrogen and wherein adjusting at least one of the polymer and the supercritical fluid comprises adjusting the concentration of the supercritical fluid added to the melted polymer to be about 0.08 wt. % to about 0.25 wt. %.

17. The method of claim 14, wherein the supercritical fluid is carbon dioxide and wherein adjusting at least one of the polymer and the supercritical fluid comprises adjusting the concentration of the supercritical fluid added to the melted polymer to be about 0.3 wt. % to about 3 wt. %.

18. The method of claim 14, wherein the supercritical fluid is carbon dioxide and wherein adjusting at least one of the polymer and the supercritical fluid comprises adjusting the concentration of the supercritical fluid added to the melted polymer to be about 0.5 wt. % to about 2 wt. %.

19. The method of claim 14, wherein adjusting at least one of the polymer and the supercritical fluid comprises adjusting a pressure drop of the supercritical fluid to be about 1 bar to about 2 bar.

20. The method of claim 14, wherein the polymer comprises low density polyethylene.

21. The method of claim 14, wherein a pressure of the single-phase polymer-gas solution prior to injecting is about 10 bar to about 200 bar.

22. The method of claim 14, wherein a pressure of the single-phase polymer-gas solution prior to injecting is about 30 bar to 100 bar.

23. The method of claim 14, wherein the plastic part is a consumer product or personal care product.

24. The method of claim 23, wherein the plastic part is a tampon applicator or an infant care product.

25. A method of molding a tampon applicator, comprising:

providing a polymer comprising a low density polyethylene resin;

heating the polymer to melt the polymer;

adding nitrogen gas to the melted polymer to produce a single-phase polymer-gas solution;

adjusting at least one of the polymer and the nitrogen gas to control at least one of a weight of the tampon applicator produced and a surface characteristic of the tampon applicator produced;

injecting the melted polymer with the nitrogen therein into a mold; and cooling the mold;

wherein injecting the melted polymer with nitrogen therein into the mold causes a pressure drop of about 0.5 bar to about 2.5 bar that causes cells of the nitrogen to nucleate in the melted polymer.

26. The method of claim 25, wherein the mass flow rate of the nitrogen added to the melted polymer is about 0.045 kg/hr to about 0.055 kg/hr.

27. The method of claim 25, wherein a pressure drop of the nitrogen is about 1 bar to about 2 bar.

28. The method of claim 25, wherein a time to add the nitrogen gas to the polymer is about 0.65 seconds to about 0.75 seconds.

* * * * *